United States Patent [19]

Straihammer et al.

[11] Patent Number: 4,983,121
[45] Date of Patent: Jan. 8, 1991

[54] DENTAL HANDPIECE

[75] Inventors: Reinhard Straihammer; Werner Schuss, both of Heppenheim; Siegfried Goisser, Einhausen; Lutz Beerstecher, Darmstadt, all of Fed. Rep. of Germany

[73] Assignee: Siemens Aktiengesellschaft, Berlin and Munich, Fed. Rep. of Germany

[21] Appl. No.: 159,754

[22] Filed: Feb. 24, 1988

[30] Foreign Application Priority Data

Feb. 26, 1987 [DE] Fed. Rep. of Germany ....... 3706263
Dec. 15, 1987 [DE] Fed. Rep. of Germany ....... 3742497

[51] Int. Cl.$^5$ ............................................... A61C 1/10
[52] U.S. Cl. ...................... 433/114; 433/126
[58] Field of Search ............... 433/126, 114, 115, 116, 433/117; 420/420

[56] References Cited

U.S. PATENT DOCUMENTS

| 3,615,378 | 10/1971 | Bomberger Jr. jet al. | 420/420 |
| 3,798,777 | 3/1974 | Reiter | 32/27 |
| 4,278,428 | 7/1981 | Straihammer et al. | 433/105 |
| 4,332,562 | 6/1982 | Schuss et al. | 433/126 |
| 4,354,839 | 10/1982 | Schuss | 433/126 |
| 4,534,732 | 8/1985 | Strohmaier | 433/126 X |
| 4,568,284 | 2/1986 | Stankiewicz | 433/126 |
| 4,578,033 | 3/1986 | Mossle et al. | 433/126 X |
| 4,642,051 | 2/1987 | Lohn | 433/126 X |
| 4,669,982 | 6/1987 | Fleer | 433/29 |
| 4,681,540 | 7/1987 | Landgraf et al. | 433/126 |

FOREIGN PATENT DOCUMENTS

| 0012872 | 7/1980 | European Pat. Off. . |
| 0029860 | 6/1981 | European Pat. Off. . |
| 0185290 | 6/1986 | European Pat. Off. . |
| 853494 | 8/1952 | Fed. Rep. of Germany . |
| 2422704 | 8/1975 | Fed. Rep. of Germany ...... 433/126 |
| 2636373 | 2/1978 | Fed. Rep. of Germany . |
| 0045943 | 2/1982 | Fed. Rep. of Germany ...... 433/114 |
| 2029232 | 3/1980 | United Kingdom . |

Primary Examiner—John Weiss
Assistant Examiner—Nicholas D. Lucchesi
Attorney, Agent, or Firm—Hill, Van Santen, Steadman & Simpson

[57] ABSTRACT

A dental handpiece is provided with a gripping sleeve, which receives a base member arrangement composed of either a single piece or multi-pieces. The base member having bearing arrangements for supporting a drive shaft section, which is engageable with the drive shaft of a motor and has an arrangement for guiding various agent lines, such as water, air or light or electrical power on the outer surface of the base member within the interior of the sleeve. The outer sleeve is free of holding and guide elements for the agent lines and the gripping sleeve can be firmly clamped onto the base member or can be clamped to the base member with interposed elastic vibration-dampening elements.

16 Claims, 2 Drawing Sheets

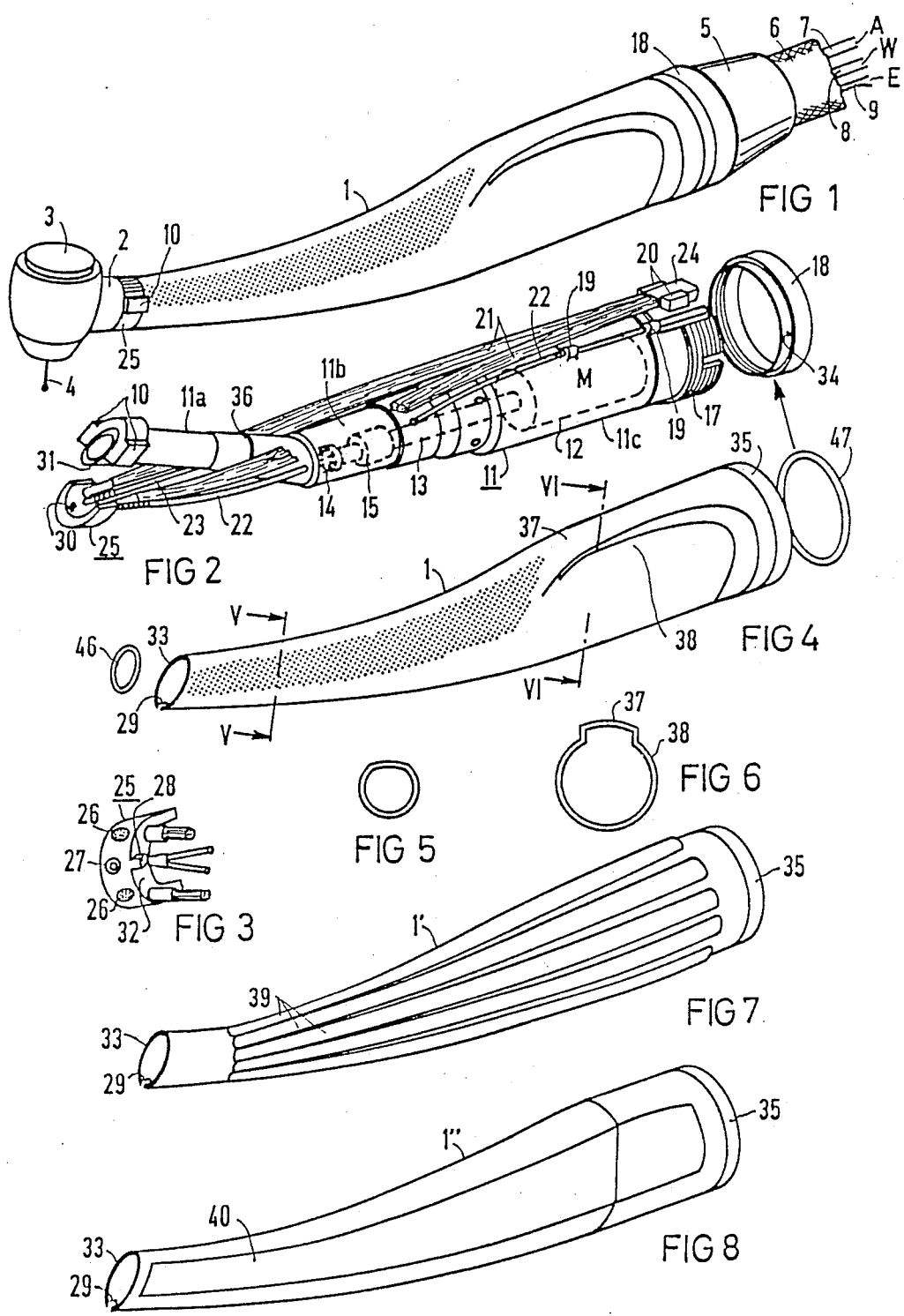

DENTAL HANDPIECE

BACKGROUND OF THE INVENTION

The present invention is directed to a dental handpiece, which is provided with a gripping sleeve and has an interior portion of a handpiece which has bearing means for supporting at least one drive shaft received in the gripping sleeve and has various lines for conducting various agents, such as air, water, electrical power or light, disposed within the gripping sleeve and extending therealong.

A dental handpiece, which has a gripping sleeve which receives a body member that has at least one drive shaft and bearing means for supporting the drive shaft, as well as various supply lines for fluids, such as air, water and power or light is disclosed in U.S. Pat. No. 4,354,839, which corresponds to European Printed Application No. 00 29 863. In this arrangement, the gripping sleeve assumes the first job of determining the outside contour with respect to the optical appearance and also the gripping properties. A second job is to receive an acceptance member or base member for the drive shaft bearings and the various agent lines.

Such an arrangement causes a comparatively complicated structure for a handpiece having a relatively high manufacturing cost, particularly for high cost of materials and also cost of machines for producing the handpiece. This outlay is especially high because a comparatively large number of parts having a high precision fit are necessary, particularly in order to provide the inwardly disposed guide channels and in order to exactly fit the inside parts of the gripping sleeve in a precise relationship to one another. In addition, the outside contour is also relatively complicated, particularly when one would like to provide handpieces with different contours.

OBJECT IF THE INVENTION

The object of the present invention is to provide a dental handpiece that is less complicated in production engineering terms, and is more economical in comparison to previously known handpieces.

A significant feature of the invention is that the gripping sleeve is practically a bare, thin sleeve, essentially only for defining the outside contour of the handpiece, and assumes no carrying function for bearings and agent lines. In contrast thereto, a basic body is a fully functional structure and is provided with all the connections for the various agents. Consequently, the gripping sleeve need only meet an enveloping function. In that the gripping sleeve is essentially supported on the base member at only two locations, preferably at the ends, and has practically no contact with the base member therebetween, one has a large free hand in view of the design of the interior structure and of the outer contour as well. In addition, a better isolation of the heat and of the structural borne sounds from the drive parts onto the gripping sleeve can be established.

With a drive arranged in the interior of the handpiece, an especially good dampening of the vibration and running noises that possibly occur can be achieved when, in accordance to an advantageous embodiment, elastic elements are provided for supporting the gripping sleeve on the base member. These elastic elements or members axially and radially fix the gripping sleeve relative to the base member so that the gripping sleeve is secured to the base member in practically a "floating" fashion. Expediently, the gripping sleeve and the base member are connected, each to one another, so that they form a solid structural unit. A structural unit that cannot be resolved by the user without further ado. The gripping sleeve is advantageously fashioned as one piece and, under certain conditions, it can also be composed of a plurality of parts that, however, form a solidly interconnected unit composed to form one piece in the assembled condition.

The handpiece will have an inside, which will contain a drive unit, such as an electrical motor, air motor, air scaler drive, and the gripping sleeve is fashioned so that it overlaps and covers this drive unit.

Since the inventive structure of the handpiece allows a large free hand with respect to the design of the outside contour, it is advantageous to allocate a plurality of gripping sleeves having different outside contours and structure to one base member so that the user can offer different handpieces with respect to the external shape, given the same identical structure of the handpiece. This is particularly important because there are frequently different ideas about the shape of a handpiece in view of this manipulation and type of preparation. These different ideas can be satisfied with comparatively little production outlay.

The gripping sleeve is advantageously composed of either a titanium alloy or can be composed of a sterilizible plastic material that may potentially comprise color identification in the form of inkings.

Other advantages and features of the present invention will be readily apparent from the following description of the preferred embodiments, the drawings and claims.

BRIEF DESCRIPTION OF THE DRAWINGS

FIG. 1 is a perspective view of a complete dental handpiece in accordance with the present invention;

FIG. 2 is a perspective view of the internal structure of the handpiece of FIG. 1;

FIG. 3 is a bottom perspective view of a connecting part illustrated in FIG. 2;

FIG. 4 is a perspective view of the gripping sleeve of the handpiece of FIG. 1;

FIG. 5 is a cross sectional view taken along the lines V—V of FIG. 4;

FIG. 6 is a cross sectional view taken along the lines VI—VI of FIG. 4;

FIG. 7 is a perspective view of an embodiment of a gripping sleeve in accordance with the present invention;

FIG. 8 is a perspective view of another embodiment of a gripping sleeve in accordance with the present invention;

DESCRIPTION OF THE PREFERRED EMBODIMENTS

Figure 9:
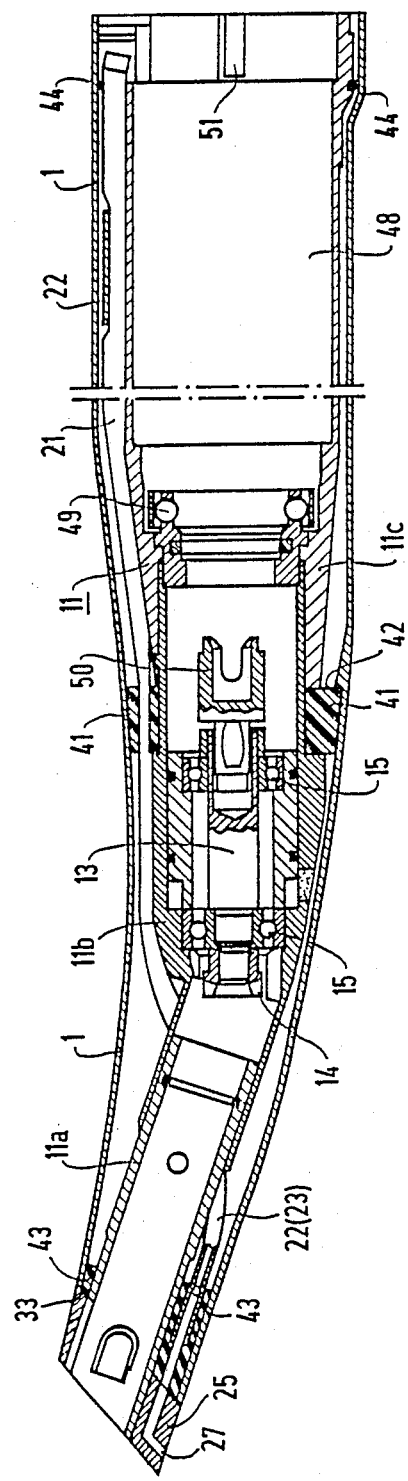
FIG. 9 is a longitudinal cross sectional view of a dental handpiece in accordance with the present invention.

The principles of the present invention are particularly useful when incorporated in a dental handpiece illustrated in FIG. 1. The dental handpiece has a gripping sleeve 1 which, at a front or first end, is connected to a head part 2 with a head housing 3. The head housing 3 contains means for mounting a tool 4, which may be a drill, miller or the like, for rotation. The dental handpiece, at the opposite or second end, has a connection fitting 5, which is for connecting a supply hose 6 to the dental handpiece. The supply hose 6 contains agent lines 7–9, such as a line 7 for air, a line 8 for water, and a line 9 for electrical energy.

The head part 2 is detachable from the remaining part of the handpiece, to which end a lock-in means (not shown in detail) can be used. Examples of the lock-in means are disclosed in copending U.S. patent application, U.S. Ser. No. 900,619, which issued as U.S. Pat. No. 4,792,304 on Dec. 20, 1988 and was based on German Patent Application No. P 35 30 424. This lock-in means is actuated by an actuation element 10, which is on the handpiece.

As best illustrated in FIG. 2, the interior of the gripping sleeve receives the interior parts of the dental handpiece. The interior parts include a base member 11, which has three sections or parts 11a, 11b and 11c, with the part 11a being offset at an angle to the parts 11b and 11c, and the part 11c has a greater diameter than 11a and has a cavity 48 (FIG. 9) for receiving a drive motor 12 (FIG. 1), which may be either an electrical motor or an air motor. A part 11b supports drive shaft bearings 15, which supports at least one drive shaft 13, which is connectible to the shaft of the motor 12 and at the other end has a gear 14, which can be engaged with a gear carried by a shaft supported in the head part 2 for transferring of the output of the motor to the tool.

At an end facing away from the head part, the base member 11, particularly the member 11c, is provided with a threaded portion 17, onto which a ring 18 can be threaded. A plurality of clamp-like supporting or, respectively, mounting elements 19 and 20 are provided on an outside periphery of the section 11c of the base member. The elements, such as 19, are used to fix or mount agent lines, such as 22 and 23, that can carry air and water to the head part 2. The elements 20 are used for mounting optical fiber bundles, such as 21, which are divided into two portions. In the illustration, the two portions 21 merge in an end part 24, which is positioned opposite an incandescent bulb, which is supplied with electrical current via the line 9 and is positioned, preferably, in the hose or connecting fitting 5. The optical fiber bundle 21 has its ends at the head part held in a connecting part 25 in which the two ends of the agent lines 22 and 23 are also secured. The connecting part 25 is constructed with a horseshoe feature and in the assembled condition, such as illustrated in FIG. 1, its outer generated surface continues the outer contour of the handpiece.

As best seen in FIG. 9, a connecting part 25 contains two exit openings 26 for the light and one exit opening 27 for both air and water. The connecting part 25 further contains a catch nose 28 on an inner end face 32. The catch nose 28 will extend axially and be engaged in a slot 29 in the first end 33 of the grip sleeve 1 (see FIG. 4) so that an anti-twist connection is formed between the part 25 and the sleeve 1.

As best illustrated in FIG. 2, the connecting part has a male member or projection 30 that is received in a bore or recess S1 arranged on the underside of the base member 11 and, thus, forms a detent. The end face 32 has a configuration to meet the oblique end 33 of the sleeve when the parts are assembled together.

The assembly of the handpiece occurs in such a fashion that insofar as dimensions allow, all of the base member 11, as shown in FIG. 2, is inserted through the sleeve, the connecting part 25 is then fixed in an anti-twist fashion by engagement of the catch nose 28 into the slot 29 and, subsequently, is clamped to the sleeve by screwing of the ring 18 onto the threads 17 of the base member. The ring 18 has an annular collar portion 34, which will be received in an expanded second end portion 35 of the sleeve. This ring 18, when firmly threaded onto the threads 17, will firmly clamp the sleeve 1 on the base member 11.

When, due to the dimensions, the base member cannot be pushed through the sleeve as a whole unit, then it is expedient to fashion the base member section 11a, 11b partable at a location 36, with this parting location being provided with means to prevent twisting between the two parts and for axial securing of the two parts in the connected location.

As illustrated hereinabove, the base member arrangement or body 11 represents a fully functional structure, but the gripping sleeve 1 carries no part whatsoever, but merely provides an enveloping function. As the cross sectional view in FIGS. 5 and 6 show, the inside of the sleeve is completely free of catch and guide elements, as well as of supporting elements for agent lines. As already set forth, the sleeve 1 is only supported on the base member 11 at its two ends and provides an inner space between the interior of the sleeve and the base member 11, in which lines, such as 21–23, can be laid arbitrarily per se to extend between the outer portions of the base member 11 and the inner surface of the sleeve 1.

The grip sleeve can have various structures. A modification of the grip sleeve, as shown by the sleeve 1' in FIG. 7, and a second modification is shown by the sleeve 1'' in FIG. 8. Both of these sleeves 1' and 1'' can be assembled onto the base member 11. These two gripping sleeves are identical to the embodiment shown in FIG. 4 only in view of their dimensions with respect to the first end 33 with the position or slot 29 and the second end 35. Otherwise, the contours differ greatly. Thus, the sleeve of FIG. 4 has a saddle or ridge 37 adjacent the back end, which saddle or ridge 37 merges with the cylindrical contour 38 to form indentations. The sleeve 1' has a plurality of flattened portions, such as 39, that extend substantially the length of the sleeve, while the sleeve 1'' has just two portions 40 that extend the length of the sleeve. Each of these structures may be better appreciated by the user than a roughened surface, which is provided on the front portion of the sleeve 1 of FIG. 4.

The handpiece structure of the present invention, thus, makes it possible to place different gripping sleeves having different shapes in view of manual holding and surface designs onto the one in the same base member. The external shape and, thus, the employment technique can, accordingly, be selected merely by changing or, respectively, selecting the suitable gripping sleeve.

The sleeves have an essentially constant, relatively thin, wall thickness in a range of 0.2–0.4 mm and are advantageously composed of a titanium alloy or of a sterilizible plastic. In the case of a titanium alloy, it is advantageous to manufacture the sleeve according to a method of super-plastic deformation, wherein an expediently prebent initial tube is placed into a die having the shape corresponding to the outer shape of the sleeve and then one end of the tube is closed and a delivery connection is attached to the other end. Gas is then introduced under pressure into the sleeve or tube, which is has been heated to the desired forming temperature so that the tube is expanded into contact with the surface of the die under the deformation of the gas pressure. After deformation and cooling, the sleeve blank is then severed at both ends to provide end surfaces, such as 33 and 35. The sleeve is then present in its completed, finished condition. In that the sleeve material is pressed against the contour of the die under pressure in its plastic deformation condition, a faultless surface design which makes no further re-working necessary, can be achieved in one work cycle.

Further discussions of this method are contained in a copending application, U.S. Ser. No. 159,753, filed Feb. 24, 1988, and assigned to the Assignee of the present application.

Instead of a titanium sleeve, the sleeve can also be produced, for example, in an injection molding process of utilizing a sterilizible plastic material. In this case, it can be advantageous to provide specific, colored markings identifying the handpiece with appropriate inkings in the injection molding process.

In order to employ the metallic gripping sleeve in combination with the drive and handpiece and to see to it that vibrations and running noises possibly coming from the drive, particularly structure-borne sounds, cannot be transmitted onto the gripping sleeve, it is proposed that the gripping sleeve be mounted to the base member 11 in a "floating" fashion. Such an embodiment of mounting is illustrated in FIG. 9.

Whereas the support of the gripping sleeve 1 at the base member 11 in the exemplary embodiment set forth before occurs in that the gripping sleeve has its oblique end surface 33 pressed against the axially latchable connecting part 25 of the base member section 11a with the assistance of a slide collar or ring 18, which is threaded onto the base member. The contact is, accordingly, established between the parts lying against one another. The support in the exemplary embodiment of FIG. 9 occurs in that a first elastic element 41 is placed on or about midway along the length of the base member 11 and has its edge lying against an internal collar 42 of the sleeve 1. Second and third elastic elements 43 and 44 are present at the two ends of the base member, respectively. These second and third elastic elements 43 and 44 see to it that the gripping sleeve is fixed to the base member in a "floating" fashion. Accordingly, no direct contact to the base member and to the connecting part 25 is established. The roughly centrally arranged element 41 is an annular-shaped part that fills out practically the full annular space between the tubular base member 11 and the internal surface of the gripping sleeve and serves, first, as an anti-twist device and, secondly, for fixing the optical fiber bundles, such as 21. The element 43 is likewise a shaped part that fills out the cavity between the base member 11 and the internal surface of the gripping sleeve, and surrounds the connecting nipple for the agent lines 22 or 23, respectively. The elastic part 44 is a simple O-ring that merely sees to it that the gripping sleeve remains a fixed distance from the base member in the back region of the handpiece adjacent the connecting member 5.

Figure 10:
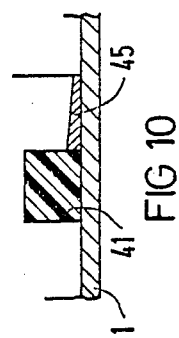
FIG. 10 is a partial enlarged cross section of an embodiment of the mounting arrangement of FIG. 9.

The collar 42, which engages the elastic element 41 for axially fixing the base member 11, can be a component part of the sleeve 1. It can also, as illustrated in FIG. 10, be formed by a separate, conical ring 45 that is secured in the sleeve 1 by, for example, gluing and/or welding.

Alternative to the design shown in FIG. 9, it is conceivable to also fashion the embodiment shown in FIGS. 2 and 4 in a floating fashion. Considering FIGS. 2 and 4, it is conceivable for this purpose to provide a first elastic element 47 at the annular expansion portion between the collar sleeve or portion 34 of the ring 18 and the corresponding surface at the face end and to provide a second elastic element in the form of an O-ring, such as 46, at the opposite end of the gripping sleeve between the slanting end surface 33 and the corresponding surface of the connecting part 25. The element 46 can be fashioned as a shaped part, as is the element 43 in FIG. 9. Such a solution, however, is not as advantageous as that set forth hereinbefore as though unambiguous axial fixing between the base member and the gripping sleeve will be established. With the presence of the parts 41 and 44 in the exemplary embodiment shown in FIG. 9, an unambiguous axial fixing will be established.

The axial clamping tensing or stressing of the parts 1 and 11 is of significance insofar as is thus possible to sterilize the base member and the gripping sleeve as a whole. To this end, the head part 2 and the connecting fitting 5 merely have to be axially withdrawn because these have been detachably secured to the base member with a lock-in mechanism in a known manner. The connecting fitting 5 advantageously also contains the drive motor 12 of FIG. 2, which is introduced cartridge-like into a space 48 (FIG. 9), which is provided for the motor and the motor is axially held with a suitable bullet catch or detent 49 in a position wherein the coupling 50 of the drive shaft 13 will be in engagement with the motor shaft. For an anti-twist fixing of the drive unit plugable into the base member 11, the base member is provided with a slot 51 into which a projection (not shown) of the cartridge for the drive unit will be engaged.

Although various minor modifications may be suggested by those versed in the art, it should be understood that we wish to embody within the scope of the patent granted hereon all such modifications as reasonably and properly come within the scope of our contribution to the art.

We claim:

1. In a dental handpiece having a head part with a head housing with a gripping sleeve extending from the head part, said handpiece having at least one drive shaft section and bearing means for supporting the drive shaft section in the interior of the handpiece, said drive shaft section having means for coupling to a drive unit and said handpiece having at least one agent line for conveying an agent the length of the dental handpiece, the improvement comprising said handpiece containing a base member arrangement having an interior passage receiving the drive shaft section and bearing means for supporting the drive shaft section, said base member arrangement at one end having means for releasably receiving said head part with the head housing, said base member arrangement having an outer surface with supporting and holding elements for securing each agent line to extend along the outer surface of the base member arrangement, said base member arrangement having a supporting location with a connecting part adjacent each end, said connecting part at said one end including a carrying part adjacent the head part, said carrying part accepting an end of each agent line having a shape for surrounding a portion of the base member arrangement and an outer contour of said carrying part extending flush with neighboring surfaces of the handpiece, said gripping sleeve having a first end and a second end, said sleeve being free of any retaining and elements for each agent line and being removably received over the base member arrangement and being in contact with the outer surface of said base member arrangement only at each of the supporting locations, said connecting parts axially clamping the gripping sleeve therebetween with said contact being in the regions of said first and second ends to form an annular interspace between an interior surface of the gripping sleeve and the outer surface of the base member arrangement in which each agent line can extend unimpeded.

2. In a dental handpiece according to claim 1, wherein the supporting location at the second end of the gripping sleeve is an annular collar allocated to the base member arrangement, said annular collar being telescopically received in the second in the second end of the gripping sleeve.

3. In a dental handpiece according to claim 2, which includes an elastic element inserted between the annular collar and the gripping sleeve.

4. In a dental handpiece according to claim 2, wherein the annular collar is a component part of a ring, said ring being threaded onto the base member arrangement.

5. In a dental handpiece according to claim 2, wherein said portion of the base member arrangement has a recess, said carrying part being received in said recess and having a projection extending into an opening in said base member arrangement, said carrying part having a surface engaging the first end of said gripping sleeve.

6. In a dental handpiece according to claim 5, wherein said carrying part contains an exit opening for each agent line, with one of said agent lines being a light waveguide.

7. In a dental handpiece according to claim 5, wherein the carrying part is constructed with a horseshoe shape.

8. In a dental handpiece according to claim 1, which includes an elastic element being positioned at each of the supporting locations, said elastic element extending between the interior of the gripping sleeve and a relative portion of the base member arrangement.

9. In a dental handpiece according to claim 8, wherein the annular elastic element disposed at the first end, which is adjacent the head housing, has an annular shape filling out the interspace between the base member arrangement and the gripping sleeve.

10. In a dental handpiece according to claim 8, wherein the gripping sleeve is provided with a seating surface, against which an elastic element is pressed to elastically fix the sleeve on the base member arrangement.

11. In a dental handpiece according to claim 10, wherein said seating surface is formed by a separate ring secured to the interior of the gripping sleeve.

12. In a dental handpiece according to claim 1, wherein a drive unit is arranged on the interior of the handpiece, said gripping sleeve being constructed to overlap the entire length of said drive unit.

13. In a dental handpiece according to claim 1, wherein a plurality of gripping sleeves having different outside contours with respectively fashioned connecting portions are allocated to a single base member arrangement.

14. In a dental handpiece according to claim 1, wherein said gripping sleeve is composed of a titanium alloy.

15. In a dental handpiece according to claim 1, wherein said gripping sleeve is preferably composed of a sterilizible plastic material.

16. In a dental handpiece having a head part with a head housing at one end and having a gripping sleeve extending from the head part, said handpiece having at least one drive shaft section and bearing means for supporting the drive shaft section in the interior of the handpiece, said drive shaft section having means for coupling to a drive unit and said handpiece having at least one agent line for conveying an agent the length of the dental handpiece, the improvement comprising said handpiece containing a base member arrangement having an interior passage receiving the drive shaft section and bearing means for supporting the drive shaft section, said base member arrangement at one end having means for forming a releasable connection to said head part and at another end having a cavity for receiving the drive unit, said base member arrangement having an outer surface with supporting and holding elements for securing each agent line to extend along the outer surface between said ends, said base member arrangement having spaced supporting locations with connecting means for axially clamping the gripping sleeve therebetween, said connecting means at said one end including a carrying part adjacent the head part, said carrying part accepting an end of each agent line and having a shape for surrounding a portion of the base member arrangement and an outer contour of said carrying part extending flush with neighboring surfaces of the handpiece, said gripping sleeve having a first end and a second end, said sleeve being free of any retaining and guide elements for each agent line and being removably received on the base member and being in contact with said base member at each of said supporting locations, said contact being limited to the regions of said supporting locations to form an annular interspace between an interior surface of the gripping sleeve and the outer surface of the base member arrangement in which each agent line can extend unimpeded.

* * * * *